(12) United States Patent
Tokarski

(10) Patent No.: US 10,006,838 B2
(45) Date of Patent: Jun. 26, 2018

(54) SAMPLING DEVICE

(71) Applicant: Adam Tokarski, Avenel, NJ (US)

(72) Inventor: Adam Tokarski, Avenel, NJ (US)

( * ) Notice: Subject to any disclaimer, the term of this patent is extended or adjusted under 35 U.S.C. 154(b) by 99 days.

(21) Appl. No.: 15/084,723

(22) Filed: Mar. 30, 2016

(65) Prior Publication Data
US 2017/0038283 A1 Feb. 9, 2017

Related U.S. Application Data

(60) Provisional application No. 62/200,799, filed on Aug. 4, 2015.

(51) Int. Cl.
G01N 1/14 (2006.01)
G01N 1/10 (2006.01)
B01L 3/02 (2006.01)
G01N 35/10 (2006.01)
G01N 1/20 (2006.01)
G01N 1/40 (2006.01)

(52) U.S. Cl.
CPC .............. G01N 1/14 (2013.01); B01L 3/0293 (2013.01); G01N 1/10 (2013.01); B01L 2400/0487 (2013.01); B01L 2400/065 (2013.01); B01L 2400/0644 (2013.01); G01N 35/1097 (2013.01); G01N 2001/205 (2013.01); G01N 2001/4088 (2013.01)

(58) Field of Classification Search
CPC ................................ G01N 1/14; B01L 3/0293
See application file for complete search history.

(56) References Cited

U.S. PATENT DOCUMENTS

| 3,918,913 A | 11/1975 | Stevenson et al. |
| 7,921,739 B2 | 4/2011 | Fjerdingstad et al. |
| 8,056,400 B2 | 11/2011 | Reintjes et al. |
| 8,074,528 B2 | 12/2011 | Zollinger |
| 8,312,780 B2 † | 11/2012 | Blacklin |
| 8,365,616 B1 † | 2/2013 | Wolcott |
| 8,789,431 B2 | 7/2014 | Blacklin et al. |

(Continued)

FOREIGN PATENT DOCUMENTS

| CN | 2446510 Y | 9/2001 |
| CN | 201579067 U | 9/2010 |

(Continued)

OTHER PUBLICATIONS

Search and Examination Report; UK Intellectual Property Office; Application No. GB1613196.3; dated Feb. 7, 2017.

Primary Examiner — Paul West
(74) Attorney, Agent, or Firm — Dunlap Bennett & Ludwig PLLC

(57) ABSTRACT

A sampling apparatus is provided. The sampling apparatus may include at least a valve, a pump and an actuator. The valve may include a sampling channel, a transfer channel and an extraction channel. The pump may be connected to at least one of the transfer channel and the extraction channel. The actuator is operable to transition the valve from a sampling position to an extracting position. The sampling position includes a fluid connection between the sampling channel and the transfer channel and the extracting position includes a fluid connection between the transfer channel and the extraction channel.

14 Claims, 4 Drawing Sheets

(56) References Cited

U.S. PATENT DOCUMENTS

2011/0107857 A1* 5/2011 Pfauch ................ G01N 27/283
　　　　　　　　　　　　　　　　　　　　　　73/866.5
2016/0243549 A1† 8/2016 Autebert

FOREIGN PATENT DOCUMENTS

| JP | S5571950 A | 5/1980 | |
|---|---|---|---|
| JP | S5740629 A | 3/1982 | |
| JP | 59190657 A * | 10/1984 | ............ G01N 30/96 |
| JP | H05142110 A | 6/1993 | |

\* cited by examiner
† cited by third party

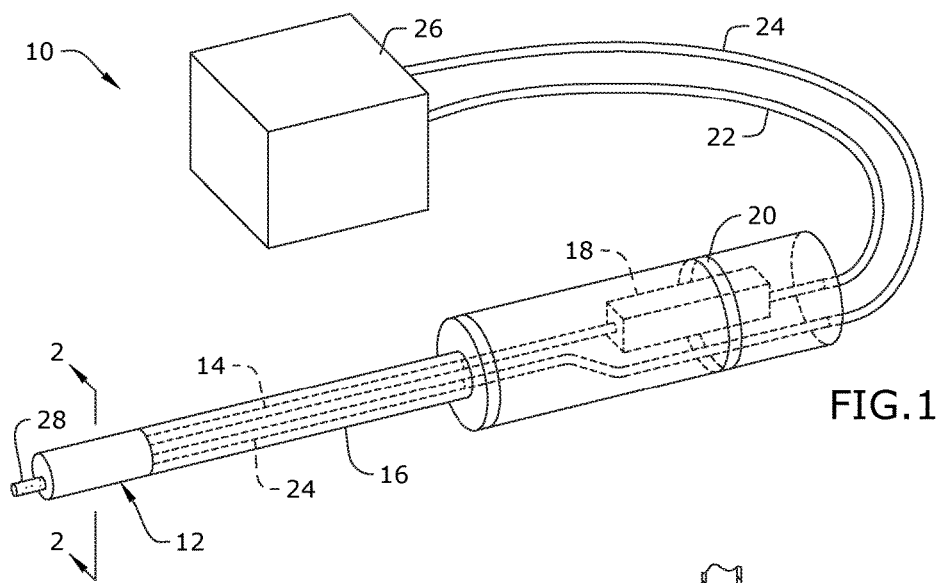
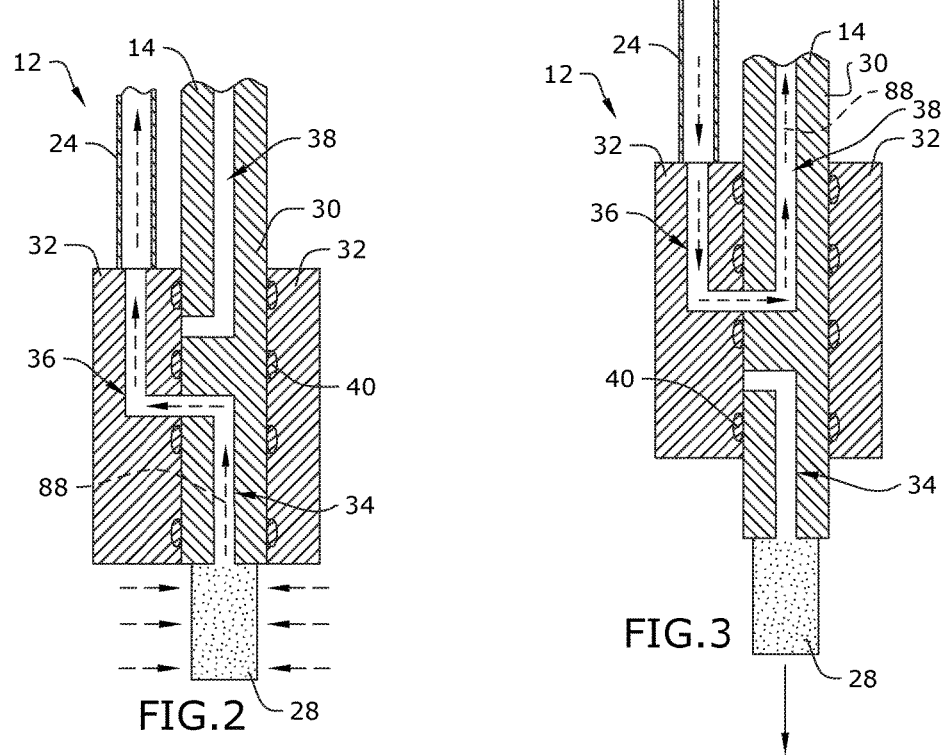
FIG.1
FIG.2
FIG.3

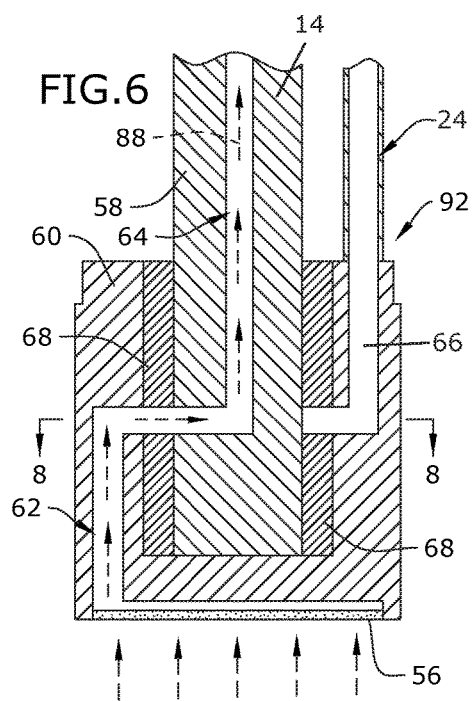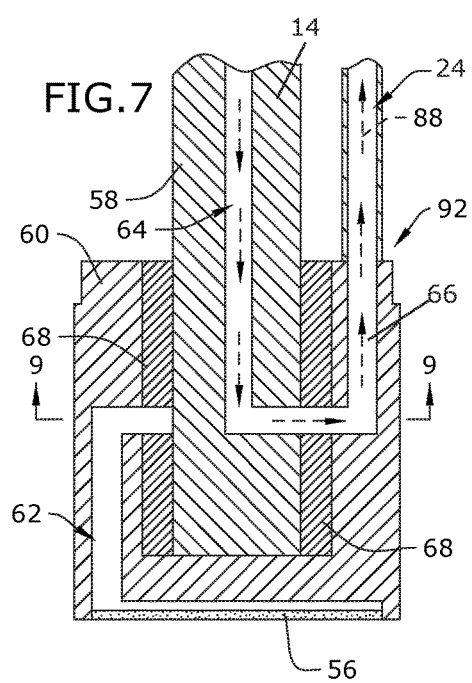

SAMPLING DEVICE

CROSS-REFERENCE TO RELATED APPLICATION

This application claims the benefit of priority of U.S. provisional application No. 62/200,799, filed Aug. 4, 2015, the contents of which are herein incorporated by reference.

BACKGROUND OF THE INVENTION

The present invention relates to sampling devices for taking liquid or slurry samples for analysis from processes media in situ, filtering solids from the sample and maintaining the sample integrity using novel mechanisms and procedures.

In fields such as physics, chemistry, or biology, in situ may describe the way a measurement is taken, that is, in the same place the phenomenon is occurring without isolating it from other systems or altering the original conditions of the test. Taking a small sample in an automated and repeated manner for analysis is a fundamental task for process monitoring. However such a task is challenging because it is hard to reach high precision, maintain the integrity of the sample and remove solids from the samples.

Sampling of laboratory vessels is typically done by a pipette. A pipette with an appropriate tip is immersed in a solution, a few micro liters are withdrawn and then deposited in a small sample bottle. In a typical chemistry laboratory, a reagent is added immediately to the sample bottle to quench the reaction and then more solvents, appropriate for subsequent analysis, are added to bring the concentration in range for the analysis. Previous efforts have not been successful for the process of monitoring laboratory vessels for the following reasons: sample volume; physical size of process; access to the process; process conditions; sample properties; maintaining sample integrity; flexibility of sampling; and preferred choice of analysis.

As can be seen, there is a need for an improved in situ sampling device.

SUMMARY OF THE INVENTION

In one aspect of the present invention, a sampling apparatus comprises: a valve comprising a sampling channel, a transfer channel and an extraction channel; a pump operable to pump fluid through at least one of the transfer channel and the extraction channel; and an actuator operable to transition the valve from a sampling position to an extracting position, wherein the sampling position comprises a fluid connection between the sampling channel and the transfer channel and the extracting position comprises a fluid connection between the transfer channel and the extraction channel.

In another aspect of the present invention, a sampling apparatus comprises: a valve comprising a valve core disposed within a valve body and comprising a sampling channel, a transfer channel and an extraction channel, wherein one of the valve core and the valve body comprises the transfer channel and the other of the valve core and the valve body comprises the sampling channel and the extraction channel; a pump operable to pump fluid through at least one of the transfer channel and the extraction channel; and an actuator connected with the valve core and operable to transition the valve from a sampling position to an extracting position, wherein the sampling position comprises a fluid connection between the sampling channel and the transfer channel and the extracting position comprises a fluid connection between the transfer channel and the extraction channel.

In another aspect of the present invention, a method of extracting a sample in situ comprises: providing a valve comprising a valve core disposed within a valve body and comprising a sampling channel, a transfer channel and an extraction channel, wherein one of the valve core and the valve body comprises the transfer channel and the other of the valve core and the valve body comprises the sampling channel and the extraction channel, wherein the valve comprises a sampling position and an extracting position, wherein the sampling position comprises a fluid connection between the sampling channel and the transfer channel and the extracting position comprises a fluid connection between the transfer channel and the extraction channel; submerging the valve within a process medium and thereby forming a thermal equilibrium between the valve and process medium; pumping a sample of the process medium through the sample channel and into the transfer channel; actuating the valve core from the sampling position to the extracting position; and pumping the sample into the extraction channel, wherein the sample is mixed with a solution in at least one of the transfer channel and the extraction channel.

These and other features, aspects and advantages of the present invention will become better understood with reference to the following drawings, description and claims.

BRIEF DESCRIPTION OF THE DRAWINGS

FIG. 1 is a perspective view of an embodiment of the present invention;

FIG. 2 is a section detail view taken along line 2-2 in FIG. 1, illustrating the present invention in a sampling position;

FIG. 3 is a section detail view taken along line 2-2 in FIG. 1, illustrating the present invention in an extracting position;

FIG. 6 is a section detail view of an embodiment, illustrating the present invention in a sampling position;

FIG. 7 is a section detail view of an embodiment, illustrating the present invention in an extracting position;

FIG. 8 is a section detail view of the present invention taken along line 8-8 in FIG. 6;

FIG. 9 is a section detail view of the present invention taken along line 9-9 in FIG. 7;

DETAILED DESCRIPTION OF THE INVENTION

Figure 4:
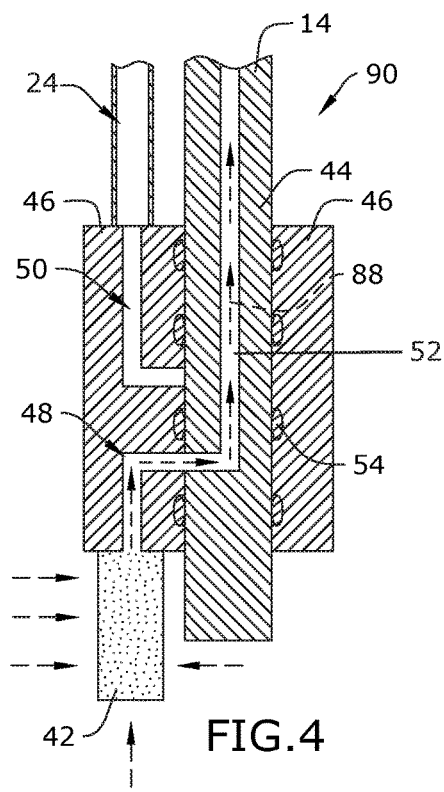
FIG. 4 is a section detail view of an embodiment, illustrating the present invention in a sampling position.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes a sampling device. The sampling device includes a specially designed valve, an actuator for operating the valve, a shaft to connect the actuator and valve, and a precision pump to draw an accurate amount of sample and deliver accurate amounts of solvent. A filter may be secured to the entrance of the valve. The filter may be made of porous, chemically and thermally inert materials.

The sampling valve of the sampling device described herein includes multiple positions. One is the sampling position at which the sampling valve opens to a process medium to allow samples be drawn through the filter by a pump through a sample channel and into a transfer channel. The transfer channel may include a solvent, thereby diluting the sample. The other position includes an extracting position. When the valve is transitioned from the sampling position to the extracting position, the valve is closed to the process medium. The transfer channel then fluidly connects to an extraction channel. The pump drives the diluted sample into the extraction channel, which may hold additional solvent, thereby further diluting the sample.

The valve of the sampling apparatus is submergible in the process medium to enable pre-treatment of the sample within the valve under the process conditions before the sample leaves the valve. An in-situ sampling methodology utilizes thermal equilibrium between the sampling valve and process medium to maintain the sample integrity under the temperature close to that of process medium after it is drawn, and pre-treat the sample before it leaves the sampling valve. Such immediate dilution before the sample leaves the sampling valve prevents the sample from precipitation, may stop a chemical reaction or may slow down degradation of analytes.

Referring to FIGS. 1 through 13, the present invention includes a sampling apparatus 10. The sampling apparatus 10 may include at least a valve 12, a pump 26 and an actuator 18. The valve 12 may include a sampling channel 34, a transfer channel 36 and an extraction channel 38. The pump 26 may be connected to at least one of the transfer channel 36 and the extraction channel 38. The actuator 18 is operable to transition the valve 12 from a sampling position to an extracting position. The sampling position includes a fluid connection between the sampling channel 34 and the transfer channel 36 and the extracting position includes a fluid connection between the transfer channel 36 and the extraction channel 38.

The sampling apparatus 10 may include the following. The actuator 18 may be housed within an actuator holder 20. The valve 12 may be connected to the actuator holder 20 by an extension rod 16. A shaft 14 may run from the actuator 18 to the valve 12 through the extension rod 16. An electrical line 22 may run from the pump 26 and connect with the actuator 18, thereby providing power to the actuator 18. A liquid line 24 may run from the pump 26, through the actuator housing 20, through the extension rod 16 and fluidly connect with the valve 12.

The pump 26 of the present invention may be a precision pump or controlled by compressed air streams. The pump 26 of the present invention may be a bi-directional pump. In such embodiments, only one pump 26 may be used to pump a sample 88 into the valve 12 and then to transfer the sample 88 from transfer channel 36 to the extraction channel 38. In certain embodiments, the present invention may utilize two different pumps 26. In such embodiments, the present invention may utilize two liquid lines 24. One of the liquid lines 24 runs from the pump 26 to the valve 12 and the other of the liquid lines 24 runs from the pump 26 to a hollow shaft 14. In such embodiments, the first pump 26 may withdraw a sample 88 into the sampling channel and into the transfer channel 36. The actuator 18 may transition the valve 12 from sampling position to the extracting position and the second pump 26 may extract the sample 88 through the extraction channel 38.

The valve 12 of the present invention may include a valve core 30 disposed within a valve body 32. In such embodiments, one of the valve core 30 and the valve body 32 includes the transfer channel 36 and the other of the valve core 30 and the valve body 32 includes the sampling channel 34 and the extraction channel 38. The actuator 18 may connect to the valve core 30 via the shaft 14. Therefore, the actuator 18 is operable to move the valve core 30 relative to the valve body 32 and thereby transition the valve 12 between positions.

The actuator 18 may be driven either electrically or by compressed air. The actuator 18 of the present invention may include a linear actuator or a rotary actuator. The linear actuator is operable to move the shaft 14 up and down, which in turn moves the valve core 30 up and down along a longitudinal axis of the valve body 32. The rotary actuator is operable to rotate the shaft 14, which in turn rotates the valve core 30 along the longitudinal axis. The rotational movement and the up and down movement transitions the valve 12 from the sampling position to the extracting position and from the extracting position to the sampling position.

The present invention may obtain a sample 88, dilute the sample 88 and then extract the diluted sample 88 for further testing. In certain embodiments, the sample 88 may be diluted twice during the extraction process. In such embodiments, a solvent may be disposed within the transfer channel 36 and the extraction channel 38. The valve 12 may be placed within the sample medium in its entirety, thereby creating an equilibrium temperature between the solvents and the sample medium. The pump 26 may extract the sample 88 from the sample medium into the sampling channel 34, which is then mixed with the solvent in the transfer channel 36. The valve core 30 is then actuated from the sampling position to the extracting position. The pump 26 transfers the diluted sample 88 into the solvent within the extraction channel 38, which further dilutes the sample 88. The pump 26 then removes the diluted sample 88 from the valve 12.

In certain embodiments, the present invention may include a filter 28, 42, 56, 70. The filter 28, 42, 56, 70 may be made of a porous, chemically and thermally resistant material. The filter 28, 42, 56, 70 may be attached to an entrance of the sampling channel 34 and may be submerged in the sample medium when taking a sample 88. The filter 28, 42, 56, 70 may be used to separate liquid from slurries.

FIGS. 2 and 3 illustrate a valve 12 utilizing a linear actuator. In such embodiments, the valve body 32 includes a top end secured to the extension rod 16, a bottom end, and a hollow core. The valve core 30 may be disposed within the hollow core of the valve body 32. O-rings 40 may be disposed in between the valve core 30 and the valve body 32 to help facilitate the linear movement of the valve core 30. The sample channel 34 may run from a tip of the valve core 30 to a side wall of the valve core 30. The transfer channel 36 may run from an inner wall of the hollow core of the valve body 32 to the top end of the valve body 32. The extraction channel 38 may be disposed above the sample channel 34 and may run from the side wall over the valve core 30 and up towards the shaft 14. The hollow shaft 14 may fluidly connect with the extraction channel 38 and the fluid line 24 may fluidly connect with the transfer channel 36. The filter 28 may be connected to an entrance of the sample channel 34. In use, the sample channel 34 is first in a position in which it is fluidly connected to the transfer channel 36. The sample 88 is pumped through the sample channel 34 and into transfer channel 36. The valve core 30 is then actuated to run downward along the longitudinal axis until the extraction channel 38 is aligned with the transfer channel 36. The sample 88 is then pumped into the extraction channel 38 and into the hollow core of the shaft 14. If a single bi-directional pump 26 is used, the final diluted solution is then pumped back into the transfer channel 36 and out to the liquid line 24. If two different pumps 26 are used, the final diluted solution may be pumped up through the shaft 14.

Figure 5:
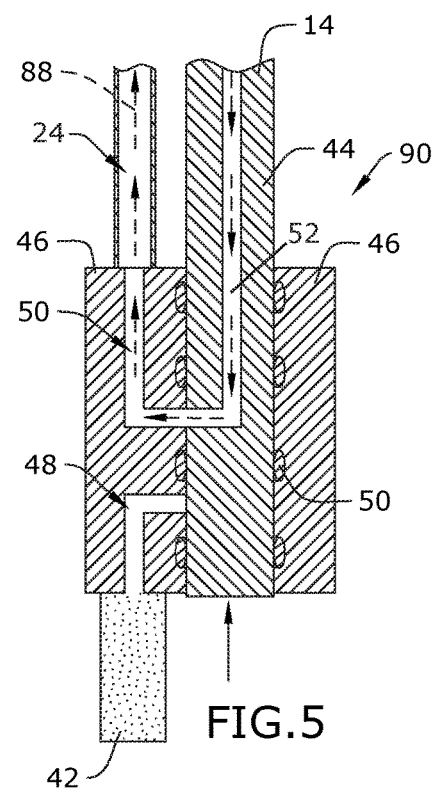
FIG. 5 is a section detail view of an embodiment, illustrating the present invention in an extracting position.
Figures 10, 11:
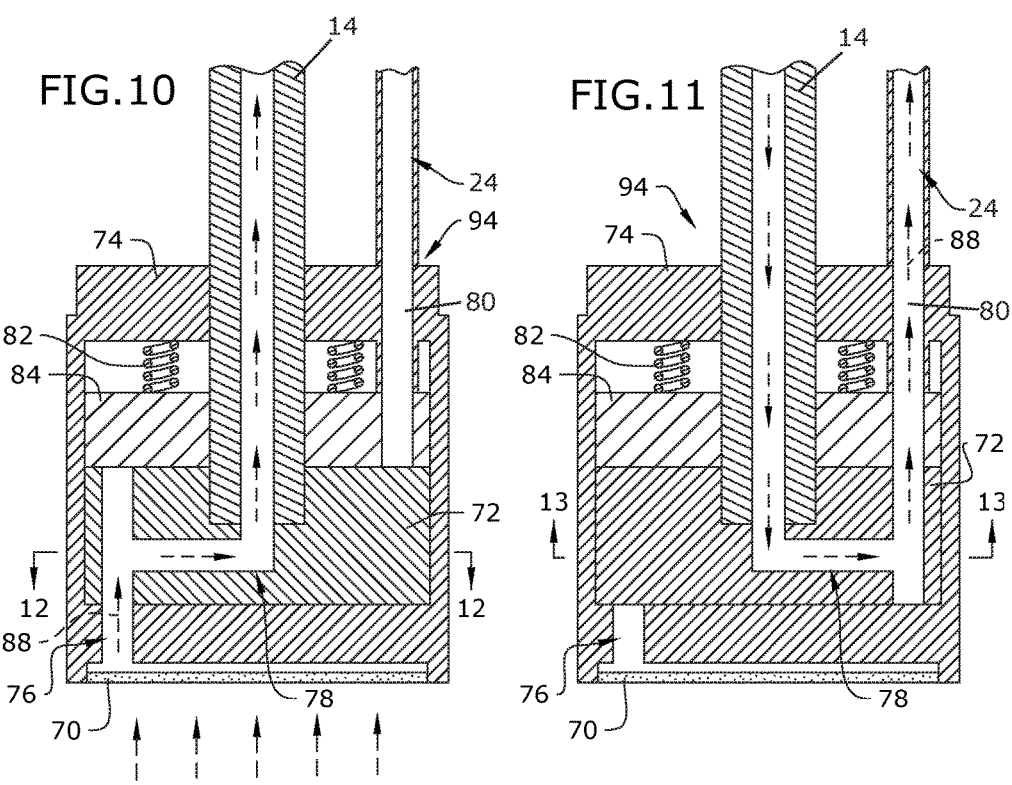
FIG. 10 is a section detail view of an embodiment, illustrating the present invention in a sampling position.
FIG. 11 is a section detail view of an embodiment, illustrating the present invention in an extracting position.
Figure 12:
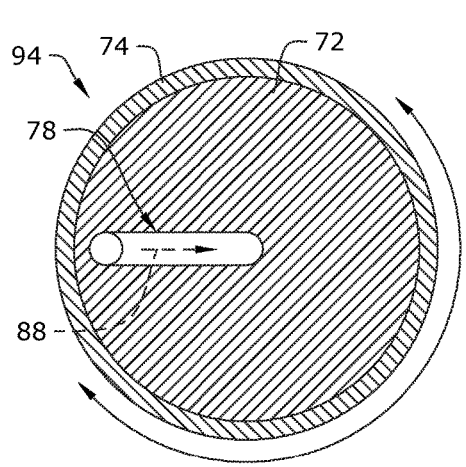
FIG. 12 is a section detail view of the present invention taken along line 12-12 in FIG. 10.
Figure 13:
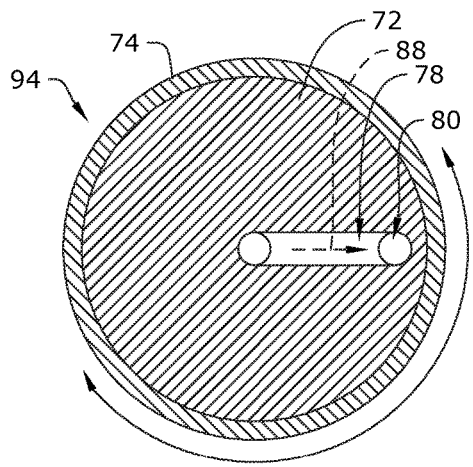
FIG. 13 is a section detail view of the present invention taken along line 13-13 in FIG. 11.

FIGS. 4 and 5 illustrate a valve 90 utilizing a linear actuator. In such embodiments, the valve body 46 includes a top end secured to the extension rod 16, a bottom end, and a hollow core. The valve core 44 may be disposed within the hollow core of the valve body 46. O-rings 54 may be disposed in between the valve core 44 and the valve body 46 to help facilitate the linear movement of the valve core 44. The sample channel 48 may run from the bottom end of the valve body 46 to the hollow core. The transfer channel 52 may run through a sidewall of the valve core 44 and run upwards towards the shaft 14. The extraction channel 50 may run from an inner wall of the hollow core of the valve body 46 to the top end of the valve body 46. The hollow shaft 14 may fluidly connect with the transfer channel 52 and the fluid line 24 may fluidly connect with the extraction channel 50. The filter 42 may be connected to entrance of the sample channel 48. In use, the sample channel 48 is first in a position in which it is fluidly connected to the transfer channel 52. The sample 88 is pumped through the sample channel 48 and into transfer channel 52. The valve core 44 is then actuated to run upward along the longitudinal axis until the extraction channel 50 is aligned with the transfer channel 52. The sample 88 is then pumped into the extraction channel 50 and into the fluid line 24.

FIGS. 6 through 9 illustrate a valve 92 utilizing a rotary actuator. In such embodiments, the valve body 60 includes a top end secured to the extension rod 16, a bottom end, and a hollow core. The valve core 58 may be disposed within the hollow core of the valve body 60. A seal 68 may be disposed in between the valve core 58 and the valve body 60 to provide a water tight seal between the channels 62, 64, 66. The seal 68 may be formed of a material with rubber elasticity, such as but not limited to, a rubber or silicone. The sample channel 62 may run from the bottom end of the valve body 60 to the hollow core. The transfer channel 64 may run through a sidewall of the valve core 58 and run upwards towards the shaft 14. The extraction channel 66 may run from an inner wall of the hollow core of the valve body 60 to the top end of the valve body 60. The hollow shaft 14 may fluidly connect with the transfer channel 64 and the fluid line 24 may fluidly connect with the extraction channel 66. The filter 56 may be connected to entrance of the sample channel 62. In use, the sample channel 62 is first in a position in which it is fluidly connected to the transfer channel 64. The sample 88 is pumped through the sample channel 62 and into transfer channel 64. The valve core 58 is then actuated to rotate along the longitudinal axis until the extraction channel 66 is aligned with the transfer channel 64. The sample 88 is then pumped into the extraction channel 66 and into the fluid line 24.

FIGS. 10 through 13 illustrate a valve 94 utilizing a rotary actuator. In such embodiments, the valve body 74 includes a top end secured to the extension rod 16, a bottom end, and a hollow core. The valve core 72 may be disposed within the hollow core of the valve body 74. A plate 84 and springs 82 are disposed within the valve body 74. The springs 82 bias the plate 84 against the valve core 72 and allow the valve core 72 to rotate, while still maintaining a water tight connection between the channels 76, 78, 80. The sample channel 76 may run from the bottom end of the valve body 60 to the valve core 72. The transfer channel 78 may run through a bottom end of the valve core 72, laterally towards a center of the valve core 72 and then upwards towards the shaft 14. The extraction channel 80 may run through the top end of the valve body 74 and align with an opening formed through the plate 84. The hollow shaft 14 may fluidly connect with the transfer channel 78 and the fluid line 24 may fluidly connect with the extraction channel 80. The filter 70 may be connected to entrance of the sample channel 76. In use, the sample channel 76 is first in a position in which it is fluidly connected to the transfer channel 78. The sample 88 is pumped through the sample channel 76 and into transfer channel 78. The valve core 72 is then actuated to rotate along the longitudinal axis until the opening of the plate 84 is aligned with the transfer channel 78. The sample 88 is then pumped into the extraction channel 80 and into the fluid line 24.

It should be understood, of course, that the foregoing relates to exemplary embodiments of the invention and that modifications may be made without departing from the spirit and scope of the invention as set forth in the following claims.

What is claimed is:

1. A sampling apparatus comprising:
   a valve comprising a valve core disposed within a valve body and comprising a sampling channel, a transfer channel and an extraction channel, wherein one of the valve core and the valve body comprises the transfer channel and the other of the valve core and the valve body comprises the sampling channel and the extraction channel;
   an actuator operable to transition the valve from a sampling position to an extracting position, wherein the sampling position comprises a fluid connection between the sampling channel and the transfer channel and the extracting position comprises a fluid connection between the transfer channel and the extraction channel; and
   at least one pump configured to draw fluid into the sampling channel to the transfer channel in the sampling position and drive the fluid from the transfer channel into the extraction channel in the extracting position.

2. The sampling apparatus of claim 1, further comprising a filter coupled to an entrance of the sampling channel.

3. The sampling apparatus of claim 1, wherein the actuator is connected to the valve core by a shaft.

4. The sampling apparatus of claim 3, wherein the actuator is a linear actuator.

5. The sampling apparatus of claim 4, further comprising a plurality of O-rings disposed in between the valve core and the valve body.

6. The sampling apparatus of claim 4, wherein the valve body comprises the transfer channel and the valve core comprises the sampling channel and the extraction channel.

7. The sampling apparatus of claim 4, wherein the valve body comprises the sampling channel and the extraction channel and the valve core comprises the transfer channel.

8. The sampling apparatus of claim 3, wherein the actuator is a rotary actuator.

9. The sampling apparatus of claim 8, further comprising a seal disposed in between the valve core and the valve body.

10. The sampling apparatus of claim 9, wherein the seal is formed of a material comprising rubber elasticity.

11. The sampling apparatus of claim 8, wherein the valve body comprises the sampling channel and the extraction channel and the valve core comprises the transfer channel.

12. The sampling apparatus of claim 8, further comprising a plate and at least one spring disposed within the valve body, wherein the spring is biasing the plate against the valve core.

13. The sampling apparatus of claim 1, further comprising a fluid line fluidly connected with the extraction channel.

14. A method of extracting a sample in situ comprising:
providing a valve comprising a valve core disposed within a valve body and comprising a sampling channel, a transfer channel and an extraction channel, wherein one of the valve core and the valve body comprises the transfer channel and the other of the valve core and the valve body comprises the sampling channel and the extraction channel, wherein the valve comprises a sampling position and an extracting position, wherein the sampling position comprises a fluid connection between the sampling channel and the transfer channel and the extracting position comprises a fluid connection between the transfer channel and the extraction channel;
submerging the valve within a process medium and thereby forming a thermal equilibrium between the valve and process medium;
pumping a sample of the process medium through the sample channel and into the transfer channel;
actuating the valve core from the sampling position to the extracting position; and
pumping the sample into the extraction channel, wherein the sample is mixed with a solution in at least one of the transfer channel and the extraction channel.

\* \* \* \* \*